(12) United States Patent
Kato

(10) Patent No.: US 7,208,514 B2
(45) Date of Patent: Apr. 24, 2007

(54) TUMORIGENESIS INHIBITOR

(75) Inventor: Norihisa Kato, Higashi-Hiroshima (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 10/548,827

(22) PCT Filed: Mar. 12, 2004

(86) PCT No.: PCT/JP2004/003315

§ 371 (c)(1),
(2), (4) Date: Oct. 6, 2005

(87) PCT Pub. No.: WO2004/080486

PCT Pub. Date: Sep. 23, 2004

(65) Prior Publication Data

US 2006/0106036 A1    May 18, 2006

(30) Foreign Application Priority Data

Mar. 13, 2003  (JP)  ............... 2003-067919

(51) Int. Cl.
*A61K 31/415* (2006.01)
(52) U.S. Cl. .................... 514/406; 548/372.5
(58) Field of Classification Search ........ 514/406; 548/372.5
See application file for complete search history.

(56) References Cited

U.S. PATENT DOCUMENTS 6,015,829 A *   1/2000   Ishibuchi et al. ........... 514/404

FOREIGN PATENT DOCUMENTS

| EP | 0 936 217 | 11/2001 |
| JP | 59-219229 | 12/1984 |
| JP | 10-310578 | 11/1998 |
| WO | 98/18765 | 5/1998 |

OTHER PUBLICATIONS

T. Tanaka et al., "Chemoprevention of Azoxymethane-Induced Rat Colon Carcinogenesis by a Xanthine Oxidase Inhibitor, 1'-Acetoxychavicol Acetate", Jpn. J. Cancer Res., vol. 88, pp. 821-830, Sep. 1997.

M. Ohnishi et al., "Chemopreventive Effect of a Xanthine Oxidase Inhibitor, 1'-Acetoxychavicol Acetate, on Rat Oral Carcinogenesis", Jpn. J. Cancer Res., vol. 87, pp. 349-356, Apr. 1996.

J. Lin et al., "Inhibition of Xanthine Oxidase and NADPH Oxidase by Tea Polyphenols", ACS Symposium Series, vol. 807, Free Radicals in Food, pp. 264-281, 2002.

* cited by examiner

*Primary Examiner*—Golam M. M. Shameem
*Assistant Examiner*—Yong Chu
(74) *Attorney, Agent, or Firm*—Wenderoth, Lind & Ponack, L.L.P.

(57) ABSTRACT

A compound having a xanthine oxidase inhibitory activity, such as 1-(3-cyano-4-neopentyloxyphenyl)pyrazole-4-carboxylic acid and the like, can be a drug for preventing cancer including colon cancer and the like, as an agent for suppressing tumorigenesis.

2 Claims, No Drawings

TUMORIGENESIS INHIBITOR

This application is a U.S. national stage of International Application No. PCT/JP2004/003315 filed Mar. 12, 2004.

TECHNICAL FIELD

The present invention relates to a novel agent for suppressing tumorigenesis.

BACKGROUND ART

As a therapeutic drug for gout and hyperuricemia, allopurinol having a xanthine oxidase inhibitory activity has been traditionally used. In addition, as compounds having a xanthine oxidase inhibitory activity, 2-phenylthiazole derivative (WO92/09279), 1-phenylpyrazole compound (WO98/18765), 3-phenylpyrazole compound (JP-A-10-310578) and the like have been reported.

It has been suggested that reactive oxygen species (ROS) is involved in pathologic symptoms of inflammation, ischemia-reperfusion injury, carcinogenesis, aging and the like (OYANAGI Yoshihiko: $O_2^-$/NO pharmacology (NIHON IGAKUKAN, 1997)). It has been further considered that xanthine oxidase (XO) is an in vivo source of ROS because it is an enzyme involved in uric acid synthesis in purine metabolism and is also involved in superoxide anion production (McCord J M: Oxygen-derived free radicals in postischemic tissue injury, N. Engl. J. Med., 312, 159–163 (1985)). Since allopurinol is known as an XO inhibitor, involvement of XO in the above-mentioned diseases has been conventionally studied using this compound. However, since allopurinol itself shows a radical removing (scavenging) effect (Moorhouse P C, Grootveld M, Halliwell B, Quinlan J G, Gutteridge J M: Allopurinol and oxipurinol are hydroxyl radical acavengers, FEBS Lett., 213, 23–28 (1987)), study of the relationship between XO and active oxygen has been difficult.

As an XO inhibitor much potent than allopurinol and free of radical scavenging effect, 1-(3-cyano-4-neopentyloxyphenyl)pyrazole-4-carboxylic acid (development code: Y-700) and the like have been recently reported and are currently under development as therapeutic drugs for gout and hyperuricemia.

However, a tumorigenesis suppressive effect, or how colon cancer is actually affected by the administration of an XO inhibitor or 1-(3-cyano-4-neopentyloxyphenyl)pyrazole-4-carboxylic acid (hereinafter to be referred to as Y-700), which is one of the XO inhibitors, has not been clarified.

DISCLOSURE OF THE INVENTION

The present inventors have set a working hypothesis that an increase in the production of ROS derived from XO is suppressed by an XO inhibitory activity and then tumorigenesis is suppressed, and conducted intensive studies and found that a compound having an XO inhibitory activity suppresses tumorigenesis, namely, suppresses formation of colon cancer, which resulted in the completion of the present invention.

Accordingly, the present invention provides a pharmaceutical agent that suppresses tumorigenesis, particularly, manifestation of colon cancer.

The present invention provides the following.

(1) An agent for suppressing tumorigenesis, which comprises a compound having a xanthine oxidase inhibitory activity.

(2) An agent for suppressing tumorigenesis, which comprises a compound having a xanthine oxidase inhibitory activity of not more than 1 μM in an $IC_{50}$ value.

(3) The agent for suppressing tumorigenesis of the aforementioned (1), wherein the compound having a xanthine oxidase inhibitory activity is a 1-phenylpyrazole compound represented by the formula (I)

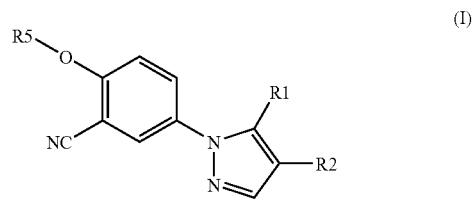

(I)

wherein $R^1$ is a hydrogen, a halogen or an amino;
$R^2$ is a carboxy or a $C_{1-4}$ alkoxycarbonyl; and
$R^5$ is a $C_{3-6}$ alkyl, a $C_{3-6}$ cycloalkyl or a $C_{3-6}$ cycloalkyl-$C_{1-4}$ alkyl, each of which is optionally substituted by 1 or 2 substituents selected from a halogen, a hydroxy, a $C_{1-4}$ alkoxy, a carboxy, a $C_{1-4}$ alkoxycarbonyl and an acyloxy, an optical isomer thereof or a pharmaceutically acceptable salt thereof.

(4) The agent for suppressing tumorigenesis of the aforementioned (1), wherein the compound having a xanthine oxidase inhibitory activity is a 3-phenylpyrazole compound represented by the formula (II)

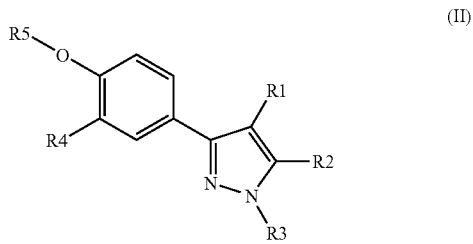

(II)

wherein $R^1$ is a hydrogen, a halogen or an amino;
$R^2$ is a carboxy or a $C_{1-4}$ alkoxycarbonyl;
$R^3$ is a hydrogen, a $C_{1-4}$ alkyl or a haloalkyl;
$R^4$ is a cyano or a nitro; and
$R^5$ is a $C_{3-6}$ alkyl, a $C_{3-6}$ cycloalkyl or a $C_{3-6}$ cycloalkyl-$C_{1-4}$ alkyl, each of which is optionally substituted by 1 or 2 substituents selected from a halogen, a hydroxy, a $C_{1-4}$ alkoxy, a carboxy, a $C_{1-4}$ alkoxycarbonyl and an acyloxy, an optical isomer thereof or a pharmaceutically acceptable salt thereof.

(5) An agent for suppressing tumorigenesis, which comprises, as an active ingredient, 1-(3-cyano-4-neopentyloxyphenyl)pyrazole-4-carboxylic acid, an optical isomer thereof or a pharmaceutically acceptable salt thereof.

(6) The agent for suppressing tumorigenesis of the aforementioned (1), wherein the compound having a xanthine oxidase inhibitory activity is 2-(3-cyano-4-isobutoxyphenyl)-4-methylthiazole-5-carboxylic acid or allopurinol.

(7) The agent for suppressing tumorigenesis of the aforementioned (1)–(6), wherein the tumor is colon tumor.

(8) An agent for the prophylaxis or treatment of colon cancer, which comprises, as an active ingredient, 1-(3-cyano-4-neopentyloxyphenyl)pyrazole-4-carboxylic acid, an optical isomer thereof or a pharmaceutically acceptable salt thereof.

BEST MODE FOR CARRYING OUT THE INVENTION

The present invention is described in detail in the following.

The definition of each symbol in the above-mentioned formulas (I) and (II) is as follows.

The halogen for $R^1$ is fluorine, chlorine, bromine or iodine.

The $C_{1-4}$ alkoxycarbonyl for $R^2$ is alkoxycarbonyl wherein the alkoxy moiety has 1 to 4 carbon atoms, such as methoxycarbonyl, ethoxycarbonyl, propoxycarbonyl, isopropoxycarbonyl, butoxycarbonyl, isobutoxycarbonyl, tertiary butoxycarbonyl and the like.

The $C_{3-6}$ alkyl for $R^5$ is a linear or branched alkyl having 3 to 6 carbon atoms, such as propyl, isopropyl, 2-ethylpropyl, butyl, isobutyl, secondary butyl, tertiary butyl, pentyl, 1-methylbutyl, 2-methylbutyl, 3-methylbutyl, neopentyl, hexyl, 2-ethylbutyl and the like. The $C_{3-6}$ cycloalkyl is cycloalkyl having 3 to 6 carbon atoms, such as cyclopropyl, cyclopentyl, cyclohexyl and the like. In addition, the $C_{3-6}$ cycloalkyl moiety of $C_{3-6}$ cycloalkyl-$C_{1-4}$ alkyl is exemplified by the same groups as mentioned above, and the $C_{1-4}$ alkyl moiety may be linear or branched and is exemplified by alkyl having 1 to 4 carbon atoms such as methyl, ethyl, propyl, butyl, isobutyl, secondary butyl, tertiary butyl and the like. Specific examples of $C_{3-6}$ cycloalkyl-$C_{1-4}$ alkyl include cyclopropylmethyl, cyclopentylmethyl, cyclohexylmethyl, 2-cyclohexylethyl, 3-cyclohexylpropyl, 4-cyclohexylbutyl and the like.

As the halogen as a substituent optionally substituted to $R^5$, fluorine, chlorine, bromine and iodine can be mentioned. The $C_{1-4}$ alkoxy is alkoxy having 1 to 4 carbon atoms, such as methoxy, ethoxy, propoxy, isopropoxy, butoxy, isobutoxy, secondary butoxy, tertiary butoxy and the like. The $C_{1-4}$ alkoxycarbonyl is alkoxycarbonyl wherein the alkoxy moiety has 1 to 4 carbon atoms, such as methoxycarbonyl, ethoxycarbonyl, propoxycarbonyl, isopropoxycarbonyl, butoxycarbonyl, isobutoxycarbonyl, tertiary butoxycarbonyl and the like. As the acyloxy, acetoxy, propionyloxy, butyryloxy, isobutyryloxy, valeryloxy, isovaleryloxy, hexanoyloxy, octanoyloxy, benzoyloxy and the like can be mentioned.

As the $C_{4-6}$ alkyl optionally substituted by 1 or 2 substituents selected from halogen, hydroxy, $C_{1-4}$ alkoxy, carboxy, $C_{1-4}$ alkoxycarbonyl and acyloxy, for example, 3-fluoro-3-fluoromethylpropyl, 3-fluoro-2,2-dimethylpropyl, 2,2-dimethyl-3-hydroxypropyl, 2,2-dimethyl-3-methoxypropyl, 2-carboxy-2-methylpropyl, 3-acetyloxy-2,2-dimethylpropyl, 3-benzoyloxy-2,2-dimethylpropyl and the like can be mentioned.

In the above-mentioned formula (II), $C_{1-4}$ alkyl for $R^3$ is alkyl having 1 to 4 carbon atoms, such as methyl, ethyl, propyl, isopropyl, butyl, isobutyl, tertiary butyl and the like and haloalkyl is a haloalkyl having 1 to 4 carbon atoms, such as trifluoromethyl, 2,2,2-trifluoroethyl, 2-fluoroethyl, 3-fluoropropyl, 1,3-difluoro-2-propyl, 4-fluorobutyl and the like. The symbols $R^1$, $R^2$ and $R^5$ are as defined above.

As $R^1$, hydrogen is particularly preferable. As $R^2$ carboxy is particularly preferable. As $R^5$, $C_{4-6}$ alkyl is particularly preferable.

As a compound encompassed in the formula (I), which has an XO inhibitory activity, the following compound can be mentioned.

A 1-phenylpyrazole compound selected from
(1) 5-amino-1-(3-cyano-4-isobutoxyphenyl)pyrazole-4-carboxylic acid,
(2) ethyl 1-(3-cyano-4-isobutoxyphenyl)pyrazole-4-carboxylate,
(3) 1-(3-cyano-4-isobutoxyphenyl)pyrazole-4-carboxylic acid,
(4) 1-(4-butoxy-3-cyanophenyl)pyrazole-4-carboxylic acid,
(5) 1-(3-cyano-4-cyclopropylmethoxyphenyl)pyrazole-4-carboxylic acid,
(6) 1-(3-cyano-4-neopentyloxyphenyl)pyrazole-4-carboxylic acid,
(7) 1-(3-cyano-4-(2-ethylbutoxy)phenyl)pyrazole-4-carboxylic acid,
(8) 1-(3-cyano-4-(1-ethylpropoxy)phenyl)pyrazole-4-carboxylic acid,
(9) 1-(3-cyano-4-(3-methylbutoxy)phenyl)pyrazole-4-carboxylic acid,
(10) 1-(3-cyano-4-((S)-2-methylbutoxy)phenyl)pyrazole-4-carboxylic acid,
(11) 5-amino-1-(3-cyano-4-neopentyloxyphenyl)pyrazole-4-carboxylic acid, and
(12) 5-chloro-1-(3-cyano-4-neopentyloxyphenyl)pyrazole-4-carboxylic acid, an optical isomer thereof or a pharmaceutically acceptable salt thereof.

As a compound encompassed in the formula (II), which has an XO inhibitory activity, the following compound can be mentioned.

A 3-phenylpyrazole compound selected from
(13) 3-(4-isobutoxy-3-nitrophenyl)pyrazole-5-carboxylic acid,
(14) methyl 3-(4-isobutoxy-3-nitrophenyl)-1-methylpyrazole-5-carboxylate,
(15) 3-(4-isobutoxy-3-nitrophenyl)-1-methylpyrazole-5-carboxylic acid,
(16) 4-chloro-3-(4-isobutoxy-3-nitrophenyl)-1-methylpyrazole-5-carboxylic acid,
(17) 3-(3-cyano-4-isobutoxyphenyl)-1-methylpyrazole-5-carboxylic acid,
(18) 3-(3-cyano-4-(2-methoxyethoxy)phenyl)-1-methylpyrazole-5-carboxylic acid,
(19) 3-(3-cyano-4-cyclopropylmethoxyphenyl)-1-methylpyrazole-5-carboxylic acid,
(20) 3-(4-butoxy-3-cyanophenyl)-1-methylpyrazole-5-carboxylic acid,
(21) 3-(3-cyano-4-isopropoxyphenyl)-1-methylpyrazole-5-carboxylic acid,
(22) 3-(3-cyano-4-cyclohexylmethoxyphenyl)-1-methylpyrazole-5-carboxylic acid,
(23) 3-(3-cyano-4-propoxyphenyl)-1-methylpyrazole-5-carboxylic acid,
(24) 3-(3-cyano-4-(3-methylbutoxy)phenyl)-1-methylpyrazole-5-carboxylic acid,
(25) 3-(4-butoxy-3-nitrophenyl)-1-methylpyrazole-5-carboxylic acid,
(26) 3-(4-isopropoxy-3-nitrophenyl)-1-methylpyrazole-5-carboxylic acid,
(27) 3-(4-(3-methylbutoxy)-3-nitrophenyl)-1-methylpyrazole-5-carboxylic acid,

(28) 3-(3-cyano-4-neopentyloxyphenyl)-1-methylpyrazole-5-carboxylic acid,
(29) 4-chloro-3-(3-cyano-4-isobutoxyphenyl)-1-methylpyrazole-5-carboxylic acid,
(30) 4-chloro-3-(3-cyano-4-neopentyloxyphenyl)-1-methylpyrazole-5-carboxylic acid,
(31) 4-amino-3-(3-cyano-4-isobutoxyphenyl)-1-methylpyrazole-5-carboxylic acid, and
(32) 4-amino-3-(3-cyano-4-neopentyloxyphenyl)-1-methylpyrazole-5-carboxylic acid, an optical isomer thereof or a pharmaceutically acceptable salt thereof.

Furthermore, the present invention encompasses the following compounds.
(33) 2-(3-cyano-4-isobutoxyphenyl)-4-methylthiazole-5-carboxylic acid,
(34) allopurinol.

As a pharmaceutically acceptable salt of the compound of the formula (I) or (II), salts with metals (sodium, potassium, calcium, lithium, magnesium, aluminum, zinc and the like) at carboxy group, and salts with organic base (diethanolamine, ethylenediamine and the like) can be mentioned.

The compounds of the formulas (I) and (II) and pharmaceutically acceptable salts thereof may be present in the form of hydrate or solvate, and these hydrates (½ hydrate, 1 hydrate, 2 hydrate and the like) and solvates are encompassed in the present invention. When the compounds of the formulas (I) and (II) have asymmetric atom(s), at least two kinds of optical isomers are present. These optical isomers and racemates thereof are also encompassed in the present invention.

The above-mentioned compounds (1)–(12) can be synthesized by the method described in WO98/18765, the compounds (13)–(32) can be synthesized by the method described in JP-A-10-310578 and compound (33) can be synthesized by the method described in WO92/09279. Allopurinol (34) is commercially available and can be obtained easily.

A compound having a xanthine oxidase inhibitory activity of not more than 1 µM ($IC_{50}$ value) has a tumor suppressive effect, or suppresses tumorigenesis, and can be used for the prophylaxis or treatment of cancer, particularly colon cancer. Preferably, 1-(3-cyano-4-neopentyloxyphenyl)pyrazole-4-carboxylic acid can be used as an agent for the prophylaxis or treatment of colon cancer.

A compound having an XO inhibitory activity, which is included in the present invention, can be administered orally and parenterally. As the dosage form for administration, tablet, capsule, granule, powder, injection and the like can be mentioned. These can be formulated into preparations by techniques generally used therefor. For example, an oral agent such as tablet, capsule, granule, powder and the like can be prepared using extenders such as lactose, crystalline cellulose, starch, vegetable oil and the like, lubricants such as magnesium stearate, talc and the like, binders such as hydroxypropylcellulose, polyvinylpyrrolidone and the like, disintegrants such as carboxymethylcellulose calcium, low substituted hydroxypropylmethylcellulose and the like, coating agents such as hydroxypropylmethylcellulose, macrogol, silicone resin and the like, film coating agents such as gelatin film and the like, and the like as necessary.

While the dose can be appropriately determined according to the symptom, age, dosage form and the like, an oral agent can be administered generally at a dose of 0.01–150 mg, preferably 0.1–100 mg, to an adult one to several times a day.

EXAMPLES

Experimental Examples and Formulation Examples are shown in the following, which aim at better understanding of the present invention and do not limit the scope of the invention in any way.

The following tests show that a compound having an XO 5 inhibitory activity has a tumorigenesis suppressive effect and is useful for the prophylaxis or treatment of cancer. As a compound having an XO inhibitory activity, Y-700 (chemical name: 1-(3-cyano-4-neopentyloxyphenyl)pyrazole-4-carboxylic acid) was used. This compound can be synthesized by the method described in WO98/18765.

Experimental Example 1

Examination of Suppressive Effect on the Formation of Azoxymethane-Induced Aberrant Crypt Foci in Colon (Experimental Method)

Y-700 was administered by feeding male ICR mice (5-week-old, 6 to 8 mice per group) for 5 weeks in a mixed diet. Azoxymethane (5 mg/kg), which is a carcinogen causing colon tumor, was subcutaneously injected once a week for 3 weeks from the start of the Y-700 administration. After the completion of the Y-700 administration, body weight, feed intake, number of colon aberrant crypt foci (ACF) and serum uric acid concentration were measured.

The group constitution was as follows.
Y-700 no addition group (control group) n=7
Y-700, 5 mg/kg mixed diet group n=6
Y-700, 10 mg/kg mixed diet group n=8
Y-700, 15 mg/kg mixed diet group n=6
Y-700, 20 mg/kg mixed diet group n=6
Diet mixing conditions: Y-700 (5, 10, 15 and 20 mg) was added 30 to 1 kg of a normal diet.

(Results and Discussion)

The results of Experimental Example 1 are shown in Table 1.

TABLE 1

| dose of Y-700 (mg/kg diet) | body weight (g) mean ± standard error | serum uric acid concentration (mg/100 ml) mean ± standard error | number of colonic ACF (n/mice) mean ± standard error |
|---|---|---|---|
| 0 | 41.1 ± 1.2 | 2.19 ± 0.27 | 10.3 ± 1.7 |
| 5 | 40.4 ± 1.2 | 1.00 ± 0.17 | 7.0 ± 1.3* |
| 10 | 39.9 ± 1.4 | 0.73 ± 0.11 | 7.0 ± 0.7 |
| 15 | 40.3 ± 0.9 | 0.84 ± 0.14 | 6.5 ± 0.6* |
| 20 | 39.9 ± 1.0 | 0.59 ± 0.15 | 5.5 ± 0.7* |

*significant difference from control group (0 mg/kg diet administration group) (Duncan's test)

Statistical analysis for significant difference in serum uric acid concentration was not performed.

No change in the feed intake was observed, nor was observed body weight change considered to be attributable to Y-700 administration. By the administration of Y-700 mixed diet, dose-dependent decreases in the serum uric acid concentration and the number of colonic ACF were seen. A very high positive correlation (r=0.97, P<0.01) was obtained between serum uric acid concentration and colonic ACF.

From the above results, it was clarified that Y-700 showed a suppressive effect on the increase in the number of colonic ACF induced by azoxymethane.

Experimental Example 2

Examination of Antioxidative Effect (Experimental Method)

Y-700 (0.5-20 μg/ml) and thiobarbituric acid (7 mg/ml) were added to a homogenate of the brain obtained from male 7-week-old Wistar rat and the mixture was incubated at 37° C. The absorbance of a thiobarbituric acid reaction product (lipid peroxide) generated 1 hr after the incubation was measured.

(Results and Discussion)

The production amount of lipid peroxide in the Y-700 addition group is shown in Table 2. The production amount of lipid peroxide is expressed in a relative percentage (%) when the absorbance of the Y-700 no addition sample was 100. No change was observed in the production amount of lipid peroxide considered to be attributable to the addition of Y-700. Therefore, Y-700 was considered to have no antioxidative effect.

TABLE 2

| Y-700 addition group (μg/ml) | relative percentage (%) when absorbance of Y-700 no addition sample is 100 (mean ± standard error, 3 tests) |
|---|---|
| 0.5 | 104 ± 7 |
| 2 | 98 ± 1 |
| 10 | 107 ± 7 |
| 20 | 96 ± 5 |

From the results of Experimental Examples 1 and 2, it was suggested that xanthine oxidase was at least partially involved in the manifestation of colon cancer, and inhibition thereof enabled prevention of manifestation of colon cancer. Since xanthine oxidase is the source of ROS, as the mechanism of suppressive effect of Y-700 on the increase in the number of colonic ACF, suppression of oxidative stress, which is based on the xanthine oxidase inhibitory activity of Y-700, is considered.

Since allopurinol known as an XO inhibitor itself shows an antioxidative effect (radical scavenging effect), it was difficult to determine whether the oxidative stress suppressive effect was mediated by xanthine oxidase or based on radical scavenging effect. The present experiments at this time suggested that Y-700 possibly suppressed carcinogenesis in colon showing no antioxidative effect. In other words, it is postulated that Y-700 suppressed an increase in the number of colonic ACF by a specific inhibitory activity against xanthine oxidase.

Experimental Example 3

Examination of Suppressive Effect on the Formation of Dimethylhydrazine-Induced Colonic ACF and Cancer Cell Growth (Experimental Method)

Y-700 mixed diet was administered to male ICR mice (5-week-old, 12 to 15 mice per group) for 10 weeks. Dimethylhydrazine (1,2-dimethyl-hydrazine, 10 mg/kg), which is a carcinogen causing colonic cancer, was subcutaneously injected once a week for 3 weeks from the start of the Y-700 administration. After the completion of the Y-700 administration, body weight, feed intake, serum uric acid concentration, number of colonic aberrant crypt foci (ACF) and growth rate of colonic mucosal cell were measured.

The group constitution was as follows.

Y-700 no addition group (control group) n=12
Y-700, 10 mg/kg mixed diet group n=13
Y-700, 20 mg/kg mixed diet group n=15
Diet mixing conditions: Y-700 (10 and 20 mg) was added to 1 kg of a normal diet.

(Results and Discussion)

The results of Experimental Example 3 are shown in Table 3.

TABLE 3

| dose of Y-700 (mg/kg diet) | serum uric acid concentration (mg/100 ml) | number of colonic ACF (n/mouse) | colonic mucosal membrane cell growth rate (% labeling index of PCNA) |
|---|---|---|---|
| 0 | 1.91 ± 0.08 | 30.7 ± 3.3 | 7.8 ± 1.4 |
| 10 | 1.08 ± 0.06* | 20.7 ± 2.0* | 4.0 ± 0.8* |
| 20 | 1.14 ± 0.07* | 22.9 ± 1.4* | 3.6 ± 1.1* | mean ± standard error
*significant difference from control group (0 mg/kg diet administration group) ($P < 0.05$, Duncan's test)

No change in the feed intake was observed, nor was observed body weight change considered to be attributable to Y-700 administration. By the administration of Y-700 mixed diet, significant decreases in the serum uric acid concentration, the number of colonic ACF and cell growth rate of the surrounding areas were observed. A very high positive correlation ($r=0.87$, $P<0.01$) was obtained between serum uric acid concentration and colonic ACF.

From the above results, it was clarified that Y-700 not only suppressed incidence of colonic ACF induced by dimethylhydrazine but also had a growth suppressive effect on colonic mucosal cells, whereby the possibility of suppression of the manifestation of colon cancer was strongly suggested.

Formulation Example 1

Tablet

| | |
|---|---|
| compound (Y-700) | 50.0 mg |
| lactose | 98.0 mg |
| corn starch | 45.0 mg |
| hydroxypropylcellulose | 3.0 mg |
| talc | 3.0 mg |
| magnesium stearate | 1.0 mg |
| | 200.0 mg |

According to the above-mentioned composition ratios, Y-700 was sufficiently kneaded with lactose, corn starch and hydroxypropylcellulose in a kneader. The kneaded product was passed through a 200 mesh sieve, dried at 50° C., and further passed through a 24 mesh sieve. The resulting product was mixed with talc and magnesium stearate and a 200 mg tablet was obtained using a 9 mm diameter punch. This tablet can be subjected to a sugar coating or film coating treatment as necessary.

INDUSTRIAL APPLICABILITY

Since a compound having a xanthine oxidase inhibitory activity has an antitumor effect, namely, it suppresses tumorigenesis and further suppresses growth of colonic mucosal cells, the compound suppresses tumorigenesis. Therefore, the pharmaceutical agent of the present invention can be used as an antitumor agent or an agent for the prophylaxis or treatment of cancer, particularly colon cancer.

This application is based on a patent application No. 2003-067919 filed in Japan, the contents of which are hereby incorporated by reference.

The invention claimed is:

1. A method for suppressing colon cancer, which comprises administering an effective amount of a compound represented by formula (I)

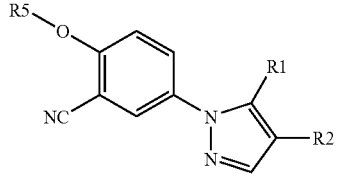

wherein $R^1$ is a hydrogen, a halogen or an amino;

$R^2$ is a carboxy or a $C_{1-4}$ alkoxycarbonyl; and $R^5$ is a $C_{3-6}$ alkyl, a $C_{3-6}$ cycloalkyl or a $C_{3-6}$ cycloalkyl-$C_{1-4}$ alkyl, each of which is optionally substituted by 1 or 2 substituents selected from a halogen, a hydroxy, a $C_{1-4}$ alkoxy, a carboxy, a $C_{1-4}$ alkoxycarbonyl and an acyloxy, an optical isomer thereof or a pharmaceutically acceptable salt thereof.

2. A method for suppressing colon cancer, which comprises administering an effective amount of 1-(3-cyano-4-neopentyloxyphenyl)pyrazole-4-carboxylic acid, an optical isomer thereof or a pharmaceutically acceptable salt thereof.

* * * * *